US00PP12977P2

(12) United States Plant Patent
Moonen

(10) Patent No.: US PP12,977 P2
(45) Date of Patent: Sep. 17, 2002

(54) VERBENA PLANT NAMED 'KIEVEREPUR'

(75) Inventor: Carla Moonen, Enkhuizen (NL)

(73) Assignee: Kieft Seeds Holland, Venhuizen (NL)

( * ) Notice: Subject to any disclaimer, the term of this patent is extended or adjusted under 35 U.S.C. 154(b) by 39 days.

(21) Appl. No.: 09/834,568

(22) Filed: Apr. 13, 2001

(51) Int. Cl.[7] ..... A01H 5/00

(52) U.S. Cl. ..... Plt./308
(58) Field of Search ..... Plt./308

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Verbena plant named 'Kieverepur', characterized by its compact, mounded and outwardly spreading plant habit; freely branching habit; dark green leaves; and white and purple bi-colored flowers.

1 Drawing Sheet

BACKGROUND OF THE INVENTION

The present Invention relates to a new and distinct cultivar of Verbena plant, botanically known as *Verbena hybrida*, and hereinafter referred to by the name 'Kieverepur'.

The new Verbena was discovered by the Inventor in 1997 as a naturally-occurring branch mutation of an unnamed *Verbena hybrida* seedling selection in a greenhouse in Venhuizen, The Netherlands. The new Verbena was selected by the Inventor on the basis of its unique flower color and compact growth habit.

Asexual reproduction of the new cultivar by terminal cuttings taken in a controlled environment in Venhuizen, The Netherlands, since the winter of 1998, has shown that the unique features of this new Verbena are stable and reproduced true to type in successive generations of asexual reproduction.

SUMMARY OF THE INVENTION

The following traits have been repeatedly observed and are determined to be the unique characteristics of 'Kieverepur'. These characteristics in combination distinguish 'Kieverepur' as a new and distinct cultivar:

1. Compact, mounded and outwardly spreading plant habit.
2. Freely branching habit.
3. Dark green leaves; densely foliated.
4. White and purple bi-colored flowers.

Plants of the new Verbena differ primarily from plants of the mutation parent in flower color and plant habit.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new Verbena.

The photograph at the top of the sheet comprises a side perspective view of a typical flowering plant of 'Kieverepur' grown in a 15-cm container for about 14 weeks.

The photograph at the bottom of the sheet comprises a close-up view of typical developing inflorescences, upper and lateral surfaces of typical inflorescences, and upper and lower surfaces of typical leaves of 'Kieverepur'.

DETAILED BOTANICAL DESCRIPTION

The cultivar Kieverepur has not been observed under all possible environmental conditions. The phenotype may vary somewhat with variations in environment such as temperature, light intensity, water status, and fertilizer rates without, however, any variance in genotype. The following observations, measurements and comparisons describe plants grown in Lompoc, Calif., under commercial practice during the summer and autumn in a polycarbonate-covered greenhouse with day temperatures about 24 to 29° C., night temperatures about 16 to 18° C. and light levels about 5,000 to 9,000 foot-candles. Unrooted cuttings were directly planted in 15-cm containers and grown for about 14 weeks and pinched twice.

In the following description, color references are made to The Royal Horticultural Society Colour Chart except where general terms of ordinary dictionary significance are used.

Botanical classification: *Verbena hybrida* cultivar Kieverepur.

Parentage: Naturally-occurring branch mutation of unnamed *Verbena hybrida* seedling selection.

Propagation:

- *Type cutting.*—Terminal cuttings.
- *Time to initiate roots.*—Summer: About 14 days at 22° C. Winter: About 21 days at 22° C.
- *Time to produce a rooted cutting or liner.*—Summer: About 21 days at 22° C. Winter: About 24 days at 22° C.
- *Root description.*—Fine, fibrous, white in color.
- *Rooting habit.*—Freely branching.

Plant description:

- *General appearance.*—Compact, mounded and outwardly spreading plant habit. Appropriate for 15-cm and larger containers.
- *Growth and branching habit.*—Vigorous and freely-branching with about 6 lateral branches, dense and bushy growth. Pinching, that is, removal of the terminal apices, enhances branching with lateral branches potentially forming at every node.

*Crop time.*—About 10 to 14 weeks are required to produce a finished flowering plant from planting an unrooted cutting in a 15-cm pot.

*Plant height.*—About 12 cm.

*Plant diameter or spread.*—About 55 cm.

*Lateral branches.*—Length: About 30 cm. Diameter: About 4 mm. Internode length: About 2.5 cm. Texture: Pubescent. Color: 146C.

*Foliage description.*—Leaves simple, opposite; generally symmetrical. Quantity: Densely foliated, about 30 leaves per lateral branch. Length: About 3.8 cm. Width: About 3 cm. Shape: Deltoid. Apex: Broadly acute. Base: Acute. Margin: Irregularly crenate. Texture: Coarse; both surfaces, pubescent. Venation pattern: Pinnate, netted. Color: Young and fully expanded foliage, upper surface: 147A; venation, 147C to 147D. Young and fully expanded foliage, lower surface: 147B; venation, 147D. Petiole: Length: About 7 mm. Diameter: About 3 mm. Color: 147D.

Flower description:

*Flower type and habit.*—Single upright salverform white and purple bi-colored flowers with light yellow to white "eye" arranged on terminal racemes; flowers sessile. Freely flowering with about 30 flower per raceme. Inflorescences positioned above and beyond the foliage. Flowers last about 5 days under greenhouse conditions. Flowers persistent. Flowers not fragrant.

*Flowering season.*—In the garden, flowering is continuous from spring until fall.

*Flower size.*—Diameter: About 2 cm. Height: About 2.8 cm. Tube length: About 2.2 cm. Throat diameter: About 2 mm.

*Flower buds.*—Rate of opening, from showing color to fully open flower: About 1 to 2 days. Length, at stage of showing color: About 1.5 cm. Diameter, at stage of showing color: About 4 mm. Shape: Tubular. Color: 77A.

*Petals.*—Quantity/arrangement: Five per flower fused at base. Lobe length: About 9 mm. Lobe width: About 1 cm. Shape: Rounded. Apex: Emarginate. Margin: Entire. Texture: Velvety, smooth. Color: When opening, upper surface: Ground color, 155B, covered with random flecks, brighter than 71A. When opening, lower surface: Ground color, 155B, covered with random flecks, 71B. Fully opened, upper surface: Ground color, 155B to 155C, covered with random flecks, 71B. With subsequent development, ground color, 155B to 155C, covered with random flecks, 77B. Fully opened, lower surface: Ground color, 155B to 155C, covered with random flecks, 71B to 71C. Throat: Towards base, 1C, towards petal lobes, 155B. Tube: 155B to 155C.

*Sepals.*—Quantity/arrangement: Five, fused into a tube. Calyx length: About 1.2 cm. Calyx diameter: About 2 mm. Shape: Elongated. Apex: Acute. Margin: Entire. Texture: Coarse; both surfaces, pubescent. Color: Upper surface: 138C. Lower surface: 137C.

*Reproductive organs.*—Stamens: Quantity: Four. Anther shape: Ovoid. Anther length: About 1 mm. Anther color: 144C. Pollen amount: Scarce. Pollen color: 144C. Pistils: Quantity: One. Pistil length: About 2 cm. Stigma shape: Bi-lobed. Stigma color: 144C. Style length: About 1.8 cm. Style color: 144D. Ovary color: 144C.

*Seed.*—None observed.

Disease/pest resistance: Plants of the new Verbena have not been observed to be resistant to pathogens and pests common to Verbena.

It is claimed:

1. A new and distinct cultivar of Verbena plant named 'Kieverepur', as illustrated and described.

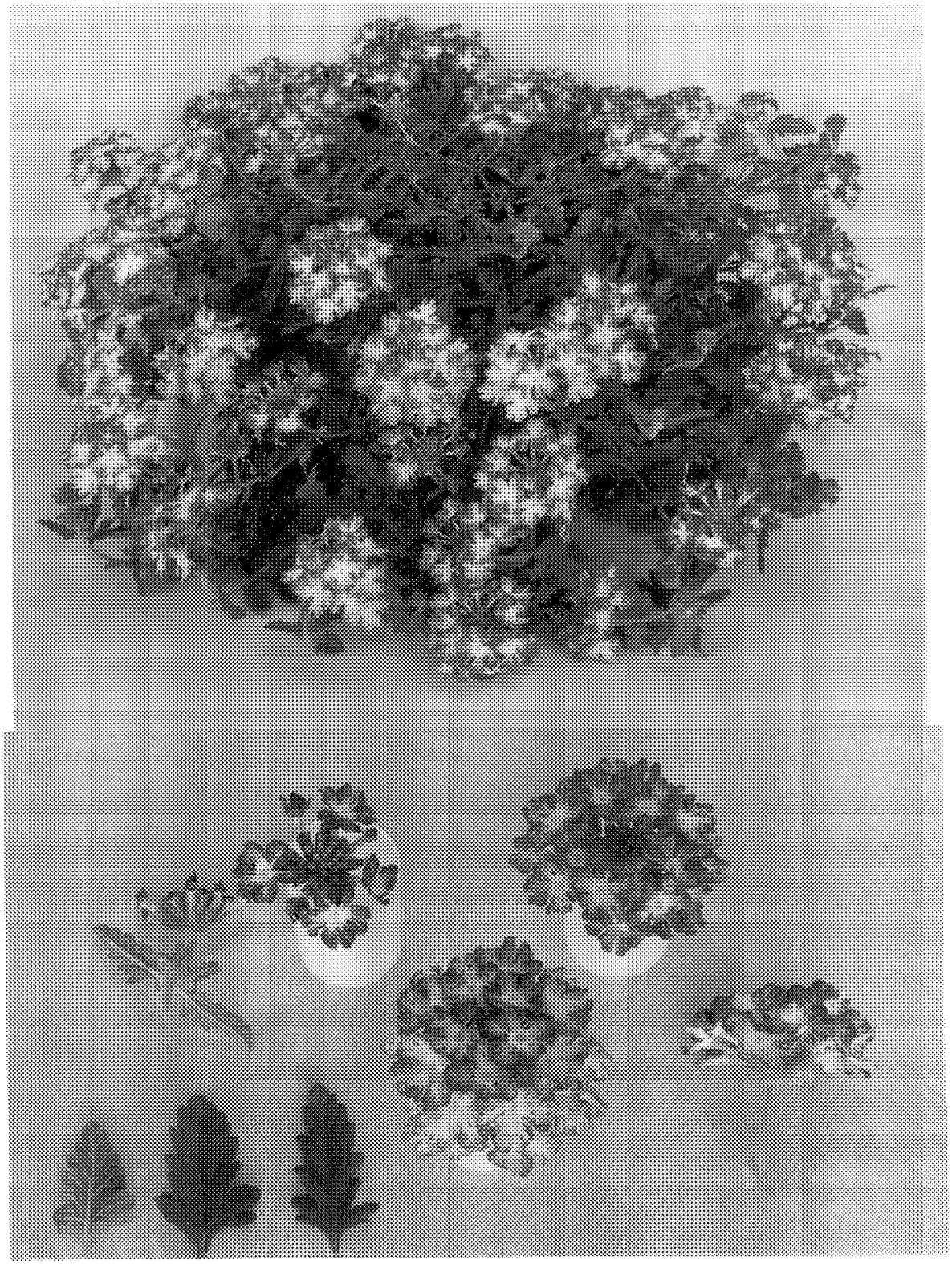

* * * * *